(12) United States Patent
Lanzetta et al.

(10) Patent No.: US 6,540,391 B2
(45) Date of Patent: Apr. 1, 2003

(54) METHOD AND APPARATUS FOR REAL-TIME DETECTION, CONTROL AND RECORDING OF SUB-CLINICAL THERAPEUTIC LASER LESIONS DURING OCULAR LASER PHOTOCOAGULATION

(75) Inventors: Paolo Lanzetta, Udine (IT); Giorgio Dorin, Cupertino, CA (US)

(73) Assignee: Iridex Corporation, Mountain View, CA (US)

( * ) Notice: Subject to any disclaimer, the term of this patent is extended or adjusted under 35 U.S.C. 154(b) by 0 days.

(21) Appl. No.: 09/844,445

(22) Filed: Apr. 27, 2001

(65) Prior Publication Data

US 2001/0046132 A1 Nov. 29, 2001

Related U.S. Application Data

(63) Continuation-in-part of application No. 60/200,709, filed on Apr. 27, 2000.

(51) Int. Cl.[7] .................................................. H01S 3/10
(52) U.S. Cl. ...................... 362/553; 362/259; 362/276; 606/11

(58) Field of Search ............................... 362/553, 259, 362/276; 606/10, 11, 12

(56) References Cited

U.S. PATENT DOCUMENTS 4,905,009 A * 2/1990 Ulich et al. .................. 342/118
6,156,030 A * 12/2000 Neev ............................ 216/94

* cited by examiner

*Primary Examiner*—Sandra O'Shea
*Assistant Examiner*—Hargobind S. Sawhney
(74) *Attorney, Agent, or Firm*—Paul Davis; Heller Ehrman White & McAuliffe

(57) ABSTRACT

An optical system is provided for use with a target site and includes a laser source producing an output beam and a reflector. A beam splitter is positioned to receive the output beam and splits the output beam into a first beam incident on the reflector and a second beam incident on at least one point of the target site. The reflector is adjustably positioned and movable along the reference optical path moveable along the reference optical path to change a length of the reference optical path.

33 Claims, 1 Drawing Sheet

METHOD AND APPARATUS FOR REAL-TIME DETECTION, CONTROL AND RECORDING OF SUB-CLINICAL THERAPEUTIC LASER LESIONS DURING OCULAR LASER PHOTOCOAGULATION

CROSS-REFERENCE TO RELATED APPLICATIONS

This application is a continuation-in-part and claims the benefit of U.S. provisional application serial No. 60/200,709, filed Apr. 27, 2000.

BACKGROUND OF THE INVENTION

1. Field of the Invention

This invention relates to an apparatus and method for detecting changes in a target site in response to interaction with a target beam of light, and more particularly to an apparatus and method for detecting real time changes in a target site in response to interaction with a target beam of coherent light.

2. Description of Related Art

Pathologies of the Eye: There are several pathologies of the eye that cause some form of visual impairment up to and including blindness. Pathologies currently treated with lasers include glaucoma and retinal disorders. Glaucoma disorders treatable with laser include open angle glaucoma, angle closure glaucoma and neovascular-refractory glaucoma. Retinal disorders treatable with laser include diabetic retinopathy, macular edema, central serous retinopathy and age-related macular degeneration (AMD), etc. Diabetic retinopathy represents the major cause of severe vision loss (SVL) for people up to 65 years of age, while AMD represents the major cause of SVL in people between 65 and 80 years of age. More than 32,000 Americans are blinded from diabetic retinopathy alone, with an estimated 300,000 diabetics at risk of becoming blind. The incidence of AMD in the USA is currently estimated at 2 million new cases per year, of which 1.8 million are with the "dry" form and 200,000 are with the "wet" form, also defined as choroidal neovascularization (CNV). CNV causes subretinal hemorrhage, exudates and fibrosis any of that can lead to SVL and legal blindness. A widely used form of laser treatment for retinal disorders is called laser photocoagulation (P.C.).

Current Modalities Of Laser P.C.: Laser P.C. has become the standard treatment for a number of retinal disorders such as diabetic retinopathy, macular edema, central serous retinopathy, retinal vein occlusion and CNV.

Laser P.C. is a photo-thermal process, in which heat is produced by the absorption of laser energy by targeted tissues, for the purpose of inducing a thermal "therapeutic damage", which causes biological reactions and ultimately, the beneficial effects. Conventional retinal P.C. relies on some visible "blanching" of the retina as the treatment endpoint and can be defined as Ophthalmoscopically Visible Endpoint Photocoagulation or OVEP. Since the retina is substantially transparent to most wavelengths used in laser P.C., its "blanching" is not caused directly by the laser. Visible "blanching" is the sign that the normal transparency of the retina has been thermally damaged by the conduction of heat generated underneath, at super-threshold level, in laser absorbing chromophores (i.e. melanin) contained in the retinal pigment epithelium (RPE) and in choroid melanocytes.

The endpoint of visible retinal "blanching" is a practical way to assess the laser treatment, but it also constitutes a disadvantageous and unnecessary retinal damage, which in turn results in a number of undesirable adverse complications including some vision loss, decreased contrast sensitivity and reduced visual fields in a substantial number of patients.

A discussion of the thermal damage resulting in the eye from laser P.C. treatment will now be presented to better illustrate the current OVEP methods, the effects, and the possible ways for limiting or avoiding the current drawbacks.

Retina "blanching" is the result of the spread by conduction of a thermal elevation created around laser absorbing chromophores underneath the retina. The thermal elevation can be controlled by laser: (i) irradiance (power density), (ii) exposure time and (iii) wavelength. High thermal elevations are normally created with current OVEP clinical protocols that are aimed to produce visible endpoints ranging from intense retinal whitening (full thickness retinal burn) to barely visible retinal changes. Although the mechanisms underpinning the efficacy of laser P.C. are still poorly understood, laser P.C. has been proven therapeutically effective and constitutes the standard-of-care in preventing SVL in various ocular disorders. However, because of the drawback of iatrogenic visual impairment due to thermal damage to the neurosensory retina, conventional OVEP laser treatment is presently considered and administered only late in the course of the disease, when has become "clinically significant" and the benefit-to-risk ratio justifies the associated negative effects.

Recent clinical studies have suggested that patients with certain types of diabetes, "dry" AMD and "wet" AMD could benefit from a much earlier treatment. As an example, Laser P.C. is now experimentally administered to patients diagnosed with "dry" AMD presenting with high-risk drusen, as a prophylactic treatment to prevent or delay the progression toward the "wet" form and the consequent SVL. Obviously, more aggressive therapeutic approaches with earlier treatments would easily gain acceptance and be adopted by the ophthalmic community if new user friendly and less damaging laser devices could be available to allow the easy administration of minimally invasive treatment protocols, which would become the new standard-of-care.

New hypotheses on the mechanism of action of laser P.C. postulate that full thickness retinal damage may not be needed to obtain beneficial effects and that any ophthalmoscopically visible retina "blanching" is only a convenient treatment end-point, redundant for the therapeutic effectiveness.

Current laser devices and treatment protocols do not allow to selectively address laser absorbing structures only (primarily melanin containing cells, such as RPE cells and choroidal melanocytes) and to confine the thermal elevation to avoid unnecessary thermal injury to the neurosensory retina. Thus, there is a need for a new laser device and treatment protocols, which can allow more selective targeting and confinement of the laser thermal effects, to avoid or minimize the thermal damage to the overlying neurosensory retina. The present invention provides the solution to this problem by providing a method and apparatus that allows the physician to perform treatments with the minimal therapeutic damage (MTD) confined around the RPE cells and without appreciable damage to the neurosensory retina. This can be defined as Non Ophthalmoscopically Visible Endpoint Photocoagulation or NOVEP treatment, to differentiate from the conventional OVEP treatment.

Preliminary studies on animals with a near IR 810 nm MicroPulse diode laser beam demonstrated the ability to consistently create therapeutic lesions confined around the RPE cells (as studied by light microscopy) without causing apparent damage to the overlying retina. The laser impacts were not visible by slit lamp bio-microscopy at the time of laser delivery.

Recent clinical studies have reported that sub-clinical (invisible) laser lesions created with a NOVEP treatment with the 810 nm MicroPulse diode laser are therapeutically as effective as the conventional OVEP treatment in resolving a variety of retinal disorders. This suggests that the damages to the neurosensory retina created with conventional OVEP treatment are indeed redundant and should be avoided. Unfortunately, the absence of a visible endpoint during the laser treatment renders difficult the choice of the proper irradiation dosage for each individual patient, leaves the physician with no tangible sign of achieved proper threshold for a MTD and creates a potential problem in case of retreatment. Thus there is a need for a device and a method that allow the real-time detection of the achieved sub-clinical (invisible) MTD during the treatment, able to control and terminate the laser emission at a given pre-settable MTD threshold. Furthermore, since from initial clinical studies it was reported that some lesions did not become apparent to slit lamp examination nor to Fluorescein Angiography even after several months, there is also a need for a device that can allow the recording of all successfully placed MTD applications and of their location in the ocular fundus.

Conventional OVEP treatment has proven to be effective in preventing or limiting SVL, but causes undesirable collateral damage. The damage of intense laser burns not only destroys healthy retinal tissue causing some degree of vision deterioration, it may also trigger neovascularization, a serious and highly undesirable event leading to further loss of vision. The mechanism by which laser P.C. leads to the beneficial therapeutic effect is poorly understood. It was believed that some damage to the retina is needed for an effective laser PC. Emerging hypotheses and recent clinical works suggest that a minimum damage, confined around the RPE and with sparing of the neurosensory retina, can suffice to trigger the pathophysiologic responses resulting in the therapeutic beneficial effects of PCT.

The threshold of cellular damage for the beneficial outcome is generally not known and many physicians striving to do no harm are now engaged in the search for the minimal dose response ("how little is enough"). The realization that "hot" laser burns can damage the integrity of Bruchs membrane and trigger iatrogenic subretinal neovascularizations has prompted the adoption of "lighter" laser PC endpoints. New NOVEP techniques, using repetitive very short laser pulses and sub-clinical (invisible) endpoints, have been advocated and clinically tried to reduce or eliminate unnecessary damage to the neurosensory retina and to Bruch's membrane. Initial results have shown therapeutically effectiveness comparable to conventional OVEP treatments.

NOVEP laser treatments are appealing, but extremely difficult to do with current laser photocoagulator devices and suffer three significant drawbacks:

(i) the lack of a visible endpoint deprive the physicians of a reassuring feedback;
(ii) the lack of visible sign of treatment makes grid treatments difficult to perform, to complete and to trace in case of retreatment
(iii) NOVEP laser lesions are spatially confined (no thermal spread as with conventional OVEP and consequently theoretically a much higher number of applications is required for the same area coverage.

There is a need for an apparatus and method for detecting real time changes in a target site in response to interaction with a target beam of coherent light. There is a further need for an apparatus and method for detecting real time changes and quantification of changes in a target site in response to interaction of the target site with a coherent beam of light. There is yet a further need for an apparatus and method for detecting real time changes, quantification of the changes and discrimination of the changes in the target site in response to interaction of the target site with a coherent beam of light.

SUMMARY OF THE INVENTION

Accordingly, an object of the present invention is to provide an apparatus and method for detecting real time changes in a target site in response to interaction with a target beam of coherent light.

Another object of the present invention is to provide an apparatus and method for detecting real time changes and quantification of changes in a target site in response to interaction of the target site with a coherent beam of light.

A further object of the present invention is to provide an apparatus and method for detecting real time changes, quantification of the changes and discrimination of the changes in the target site in response to interaction of the target site with a coherent beam of light.

These and other objects of the present invention are achieved in an optical system for use with a target site that includes a laser source producing an output beam and a reflector. A beam splitter is positioned to receive the output beam and splits the output beam into a first beam incident on the reflector and a second beam incident on at least one point of the target site. The splitter is positioned to define a target site optical path from the splitter to the target site and a reference optical path from the splitter to the reflector. The splitter produces a combined beam from at least a portion of a reflected first beam received from the reflector that interacts with at least a portion of a reflected second beam received from the target site. A detector is coupled to the splitter and produces a signal representative of a longitudinal reflectivity profile of the target site. A feedback is coupled to the detector and the laser source. The feedback provides an a feedback signal to the laser source that controls an energy output of the laser source.

In another embodiment of the present invention, a method of detecting changes in a target site in response to interaction with a target beam of light splits an output beam from a laser source into a first beam and a second beam. The first beam is directed to a reflector which reflects a reflected first beam. The second beam is directed to a target site. At least a portion of the second beam creates a change in the target site and at least a portion is reflected from the target site as a reflected second beam. The first and second reflected beams are combined and interferometrically interacted. The output beam is adjusted in response to the interferometric interaction of the first and second reflected beams.

DETAILED DESCRIPTION

Figure 1:
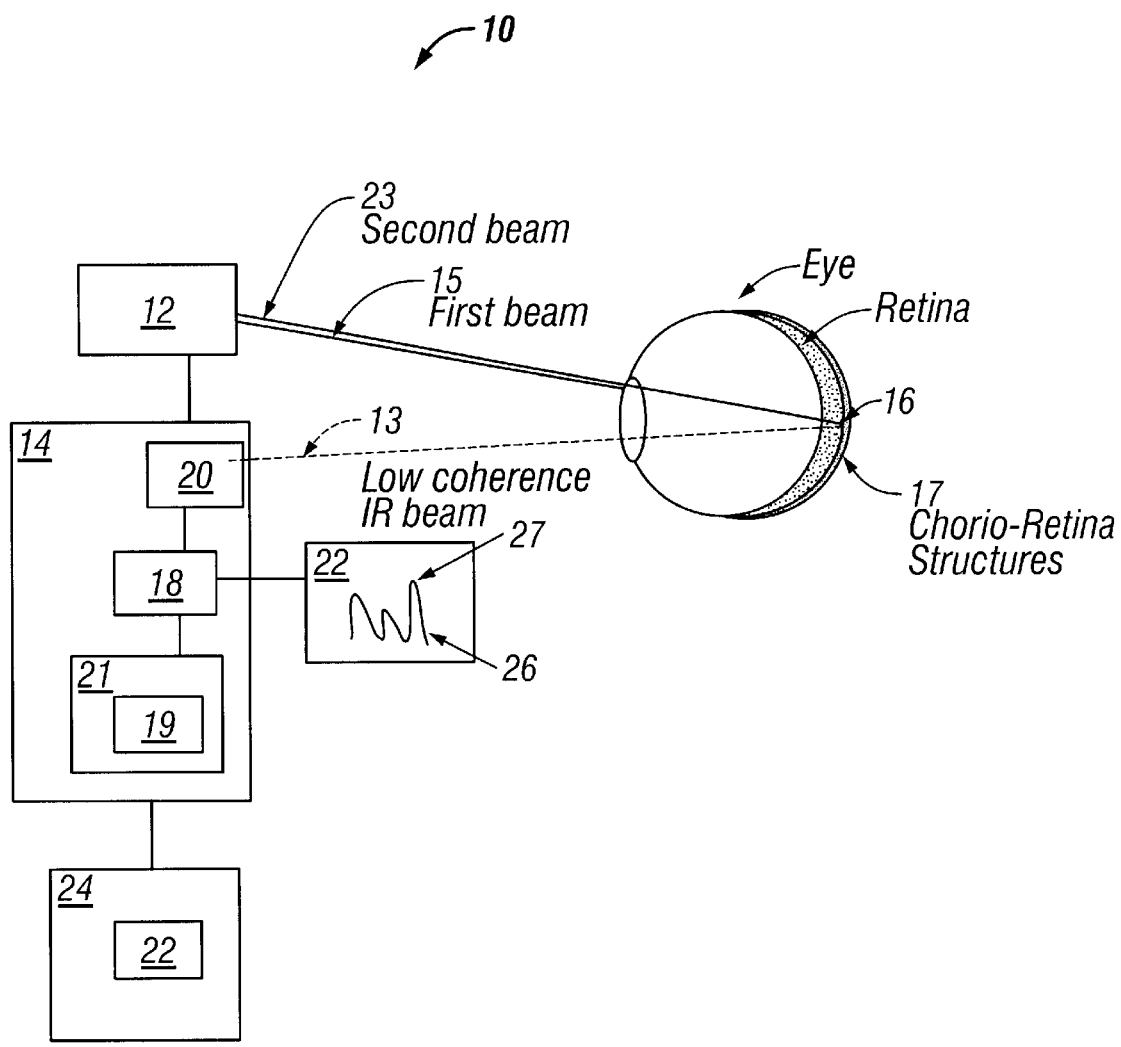
FIG. 1 is a schematic view of an embodiment of the invention.

In one embodiment of the present invention, an optical system is provided for use with a target site and includes a laser source producing an output beam and a reflector. A beam splitter is positioned to receive the output beam and splits the output beam into a first beam incident on the reflector and a second beam incident on at least one point of the target site. The reflector is adjustably positioned and movable along the reference optical path moveable along the reference optical path to change a length of the reference optical path.

The splitter is positioned to define a target site optical path from the splitter to the target site and a reference optical path from the splitter to the reflector. The splitter produces a combined beam from at least a portion of a reflected first beam received from the reflector that interacts with at least a portion of a reflected second beam received from the target site. A detector is coupled to the splitter and produces a signal representative of a longitudinal reflectivity profile of the target site. A feedback is coupled to the detector and the laser source. The feedback provides an a feedback signal to the laser source that controls an energy output of the laser source.

In another embodiment of the present invention, a method of detecting changes in a target site in response to interaction with a target beam of light splits an output beam from a laser source into a first beam and a second beam. The first beam is directed to a reflector which reflects a reflected first beam. The second beam is directed to a target site. At least a portion of the second beam creates a change in the target site and at least a portion is reflected from the target site as a reflected second beam. The first and second reflected beams are combined and interferometrically interacted. The output beam is adjusted in response to the interferometric interaction of the first and second reflected beams.

At least a portion of the splitter and/or detector can be a reflectometry device. The splitter and detector interferometrically reconstruct the reflected second beam received from the target site. The reflected first beam experiences time delays which interact interferometrically with different reflection phases of the reflected second beam at the splitter and detector.

The splitter and detector create a sequence of longitudinal reflectivity profiles at a high repetition rate. The detector continuously analyzes the longitudinal reflectivity profiles. Changes in the longitudinal reflectivity profiles above a threshold result in an adjustment in the amount of power delivered from the laser source. The splitter and detector provide real time detection, quantification and discrimination of changes in the target site in response to interaction of the first beam at the target site.

The longitudinal reflectivity profiles provide information about changes in layers of the target site at and below a surface of the target site. The longitudinal reflectivity profiles are represented as a plurality of graphed peaks. The detector detects changes in a height, width and area of one or more of the graphed peaks. Continuos analysis of the longitudinal reflectivity profiles provides a real time detection of changes in the target site. Analysis of the longitudinal reflectivity profiles provides a real time detection of changes in different layers of the target site.

Referring to FIG. 1, an embodiment of an apparatus 10 for treating ocular pathologies includes a laser photocoagulator device 12 which includes a slit lamp delivery system coupled to an interferometric reflectometry device 14 for performing real-time detection of sub-clinical laser P.C.. Interferometric reflectometry device 14 (also called reflectometry device 14) can be configured to be both optically and electronically coupled to photocoagulator device 12 for performing real-time control and recording of sub-clinical laser P.C..

Photocoagulator device 12 is configured to produce a tissue photothermal effect within a targeted ocular tissue site 16 as a result of incident laser energy on the ocular tissue. In an embodiment, photocoagulator device 12 can be a laser device known in the art. Examples of lasers include, but are not limited to, Argon lasers, Krypton lasers, Dye lasers, YAG lasers, frequency-doubled Nd:YAG lasers, Diode visible and infrared lasers, etc. Laser device 12 can include both an aiming beam and a treatment beam which can have the same or a different wavelength. Other examples of photocoagulator devices include but are not limited to infrared lamps, flash lamps, mercury vapor lamps and the like. For ease of discussion photocoagulator device 12, will now be referred to as laser 12.

The reflectometry device 14 is configured to detect, control and record laser induced therapeutic sub-clinical (opthalmoscopically invisible) lesions, during the treatment of various ocular disorders with laser 12. Reflectometry device 14 can be further configured to control the proper dose of laser energy (exposure time and/or number of ultra-short repetitive pulses) to be delivered to the target ocular tissue 16, sufficient for a desired and pre-settable MTD threshold. In an embodiment, reflectometry device 14 can include logic resources 18 that can be coupled to one or more optical sensing devices 20. Examples of logic resources 18 include digital computers and microprocessors such as a Pentium® family microprocessor manufactured by the Intel® Corporation (Santa Clara, Calif.). Examples of optical sensing device include photomultipliers, photodiodes and CCDS (charged coupled device). The optical sensing device is coupled to a slit lamp delivery system and is part of the low-coherence interferometer with filters, beam splitter, lenses, scanning and deflecting mirrors of the reflectometry device 14.

Logic resources 18 can be programmed to detect, control and record the delivery of energy to target tissue. This can be accomplished through the use of one or more electronic instructions sets or software programs 19 electronically stored or in electronic communication with logic resources 19. Logic resources 18 can also include or be coupled to memory resources 21 configured to store programs 19, data, data sets and databases. Examples of programs 19 include control algorithms such as proportional, proportional derivative and proportional derivative integral (PID) algorithms. Examples of memory resources 21 include RAM, ROM, PROM and flash memory. Examples of data and databases that can be stored include optical interference patterns and profiles data and other optical data. A database of such information can be both for a population or an individual patient and may include baseline (e.g. pretreatment), treatment and post-treatment profiles.

Reflectometry device 14 including logic resources 18 can also be coupled to a display device 22 so as to display real time or stored measurements and data generated by reflectometry device 14. In an embodiment display device 22 is configured to display all the locations within the ocular fundus where a change in the longitudinal reflectivity profile (LRP) described herein has reached a set MTD threshold. Examples of display devices 22 include cathode ray tubes (CRTs), liquid crystal displays, plasma displays, flat panel displays and the like. Display device 22 can also be incorporated in an external computer/printer 24, coupled to reflectometry device 14.

In various embodiments, reflectometry device 14 can have an integrating sphere, annular, ellipsoidal, totally or partially reflecting mirrors configuration, fiber optic Michelson interferometer or other configuration known in the art.

Also reflectometry device 14 can have both a probe (e.g. sample) and a reference beam. In an embodiment, the probe and the reference beams can be generated using a low-coherence IR diode laser device integral to or otherwise optically coupled to reflectometry device 14 and/or laser device 12.

Reflectometry device 14 is used to non-invasively detect, monitor, analyze and compare the changes of the reflectance properties of the ocular fundus occurring during the treatment with laser 12 or another eye treatment device or method. Specifically, reflectometry device 14 is configured to direct a low-cohernce IR laser beam 13 through the retina to interact with several chorio-retina structures 17 in ocular tissue 16. The back-scattered light from these interactions can be interferometrically reconstructed by reflectometry device 14 and/or logic resources 19 to generate a sequence of longitudinal reflectivity profiles (LRP) 26 at very high repetition rate. All LRPs are continuously analyzed and the occurrence of changes above an adjustable value (the MTD threshold) threshold are detected, processed for on-line control of the emission of laser 12, and stored on computer 24 and/or on memory resources 21 for recording all successful applications, their location and other relevant data pertaining to the treatment. The LRP enables different retinal and sub-retinal tissue layers to be recognizable by their reflectivity "signature". Any change occurring in one of these layers due to the laser treatment will cause a change in the LRP. Therefore, monitoring LRP change allows the real-time detection of minute changes induced in sub-retinal structures by the NOVEP laser treatment, even when they are sub-clinical and not visible to the surgeon. In this invention, an adjustable threshold of LRP change is used to detect and electronically process the achievement of a desired sub-clinical MTD threshold. Specifically, laser photocoagulation therapy causes cellular and morphological changes to the target ocular tissue/structures, which in turn result in changes to the optical properties of these structures and hence in their interferometric reflectivity signature. These changes can be detected and quantified by continuously analyzing changes occurring in the sequence of LRPs taken at high sampling rate during the laser treatment. Quantification of the amount of changes can be made through comparison and analysis of the height, width and area of one or more peaks 27 in the sequence of subsequent LRPs 26. In related embodiments, the amount of laser induced cellular change can be determined using a polynomial equation using as variables one or more characteristics of one or more of the LRP's peaks.

The desired amount of LRP change, correlated to clinically established therapeutically effective cellular changes, can be preset accordingly with the condition to be treated. This change in LRP can be used as the endpoint for the NOVEP treatment. The detection of a certain threshold of LRP change (e.g. changes in number of peaks as well as peak width, height etc.) can be used to automatically terminate the laser emission and/or to provide the surgeon with a perceptible endpoint signal. Specifically, reflectometry device 14 can be configured (through software programs 19 operating on logic resources 18 or other electronic control means) to control the duration and/or the number of repetitive pulses of the laser irradiation by laser 12. In this way, the laser emission can be stopped at the first detection of a preset therapeutically sufficient cellular change (the MTD threshold), much earlier than the appearance of an indirect thermal injury to the retina up to and including an opthalmoscopically visible "blanching".

As described herein all LRPs changes over a preset adjustable threshold (successful treatment) can be digitally stored with the coordinates of their retinal location on computer 24. These stored LRPs data can be further mapped (otherwise correlated) onto an image of the retina, retinal fundus or other structure of the eye. The mapping can be accomplished via digital manipulation, imaging processing or other computation means or manually. In various embodiments these mapping method can be used to record the amount/threshold of LRP change associated with all the successfully delivered NOVEP laser applications and the coordinates of their locations within the eye and/or in relation to the retinal fundus for a particular patient or a patient population. These stored LRP scans can be used to generate a database of invisible laser treatment endpoints accomplishment in various locations within the retina, retinal fundus or other structure of the eye.

In use, reflectometry device 14 allows:
  (i) detection of sub-clinical (ophthalmoscopically invisible) cellular and morphological changes occurring at the time of therapeutic NOVEP laser treatment;
  (ii) quantification of laser induced changes compared to preset adjustable change thresholds, to signal the achievement of a desired minimum treatment level (MTD);
  (iii) automatic control of the termination of laser emission;
  (iv) recording of all successful applications, their retinal locations and other relevant data pertaining to the treatment. Further, apparatus 10 and reflectometry device 14 allow for the titration of laser NOVEP treatment to a desired clinical endpoint (the minimum therapeutically effective cellular change) without causing unwanted thermal damage to important structures of the eye such as the neurosensory retina.

The foregoing description of various embodiments of the invention has been presented for purposes of illustration and description. It is not intended to limit the invention to the precise forms disclosed. Obviously, many modifications, variations and different combinations of embodiments will be apparent to practitioners skilled in the art. Also, it will be apparent to the skilled practitioner that elements from one embodiment can be readily recombined with one or more other embodiments.

What is claimed is:

1. An optical system for use with a target site, comprising:
 a probe laser source producing an output beam;
 a reflector;
 a beam splitter positioned to receive the output beam and split the output beam into a first beam incident on the reflector and a second beam incident on at least one point of the target site, the splitter being positioned to define a target site optical path from the splitter to the target site and a reference optical path from the splitter to the reflector; the splitter producing a combined beam from at least a portion of a reflected first beam received from the reflector that interacts with at least a portion of a reflected second beam received from the target site;
 a detector coupled to the splitter and producing a signal representative of a longitudinal reflectivity profile of the target site; and
 a feedback coupled to the detector and the laser source to provide a feedback signal that permits control of an energy output of the laser source.

2. The system of claim 1, wherein at least a portion of the splitter is a reflectometry device.

3. The system of claim 1, wherein at least a portion of the detector is a reflectometry device.

4. The system of claim 1, wherein the splitter and detector interferometrically reconstruct the reflected second beam received from the target site.

5. The system of claim 1, wherein reflected first beam experiences time delays which interact interferometrically with different reflection phases of the reflected second beam at the splitter and detector.

6. The system of claim 1, wherein the splitter and detector create a sequence of longitudinal reflectivity profiles at a high repetition rate.

7. The system of claim 6, wherein the detector continuously analyzes the longitudinal reflectivity profiles.

8. The system of claim 6, wherein changes in the longitudinal reflectivity profiles above a threshold result in an adjustment in the amount of power delivered from the laser source.

9. The system of claim 7, wherein the longitudinal reflectivity profiles provide information about changes in layers of the target site at and below a surface of the target site.

10. The system of claim 7, wherein the continues analysis of the longitudinal reflectivity profiles provides a real time detection of changes in the target site.

11. The system of claim 7, wherein the continues analysis of the longitudinal reflectivity profiles provides a real time detection of changes in different layers of the target site.

12. The system of claim 6, wherein the longitudinal reflectivity profiles are represented as a plurality of graphed peaks.

13. The system of claim 12, wherein the detector detects changes in a height, width and area of one or more of the graphed peaks.

14. The system of claim 1, wherein the splitter and detector provide real time detection of changes in the target site in response to interaction of the first beam at the target site.

15. The system of claim 1, wherein the splitter and detector provide real time detection and quantification of changes in the target site in response to interaction of the first bean at the target site.

16. The system of claim 1, wherein the splitter and detector provide real time detection, quantification and discrimination of changes in the target site in response to interaction of the first beam at the target site.

17. The system of claim 1, wherein the reflector is adjustably positioned at the reference optical path.

18. The system of claim 17, wherein the reflector is moveable along the reference optical path.

19. The system of claim 17, wherein the reflector is adjustably positioned to change a length of the reference optical path.

20. The system of claim 19, wherein the at least a portion of the reflected first beam experiences time delays which interact interferometrically with different reflection phases of the target site.

21. The system of claim 19, wherein the at least the portion of the reflected first beam experiences time delays which interact interferometrically with different reflection phases of the at least the portion of the reflected second beam received from the target site.

22. The system of claim 1, wherein the feedback signal permits a manual control of the energy output of the laser source.

23. The system of claim 1, wherein the feedback signal permits a automatic control of the energy output of the laser source.

24. A method of detecting changes in a target site in response to interaction with a target beam of light, comprising:
    splitting an output beam from a laser source into a first beam and a second beam;
    directing the first beam to a reflector which reflects a reflected first beam;
    directing the second beam to a target site, at least a portion of the second beam creating a change in the target site and at least a portion being reflected from the target site as a reflected second beam;
    combining the first and second reflected beams;
    interferometrically interacting the first and second reflected beams; and
    adjusting the output beam in response to the interferometric interaction of the first and second reflected beams.

25. The method of claim 24, wherein the first beam experiences time delays which interact interferometrically with different reflection phases of the reflected second beam.

26. The method of claim 24, further comprising:
    creating a sequence of longitudinal reflectivity profiles of the target site in response to interferometrically interacting the first and second reflected beams.

27. The method of claim 26, further comprising:
    analyzing the longitudinal reflectivity profiles.

28. The method of claim 27, wherein power delivered from the laser source is adjusted in response to changes in the longitudinal reflectivity profiles above a threshold.

29. The method of claim 27, wherein the longitudinal reflectivity profiles provide information about changes in the target site resulting from interaction of the target site with the second beam.

30. The method of claim 27, wherein analysis of the longitudinal reflectivity profiles provides a real time detection of changes in the target site resulting from interaction of the target site with the second beam.

31. The system of claim 27, wherein the analysis of the longitudinal reflectivity profiles provides a real time detection of changes in different layers of the target site.

32. The system of claim 27, wherein the analysis of the longitudinal reflectivity profiles provides real time detection and quantification of changes in the target site in response to interaction of the first beam at the target site.

33. The system of claim 27, wherein the analysis of the longitudinal reflectivity profiles provides real time detection, quantification and discrimination of changes in the target site in response to interaction of the first beam at the target site.

* * * * *